(12) United States Patent
Iketani et al.

(10) Patent No.: US 7,766,818 B2
(45) Date of Patent: Aug. 3, 2010

(54) ELECTRONIC ENDOSCOPE SYSTEM

(75) Inventors: Kohei Iketani, Saitama (JP); Mitsufumi Fukuyama, Hyogo (JP)

(73) Assignee: Hoya Corporation, Tokyo (JP)

( * ) Notice: Subject to any disclaimer, the term of this patent is extended or adjusted under 35 U.S.C. 154(b) by 532 days.

(21) Appl. No.: 11/383,367

(22) Filed: May 15, 2006

(65) Prior Publication Data
US 2006/0256191 A1 Nov. 16, 2006

(30) Foreign Application Priority Data
May 16, 2005 (JP) .......................... P2005-142536

(51) Int. Cl.
*A61B 1/04* (2006.01)
(52) U.S. Cl. .................... 600/118; 600/109; 600/160; 600/178; 348/65
(58) Field of Classification Search ................ 600/109, 600/160, 178, 407, 476, 477; 348/65, 68–71, 348/74
See application file for complete search history.

(56) References Cited

U.S. PATENT DOCUMENTS

| | | | | |
|---|---|---|---|---|
| 5,164,824 A | * | 11/1992 | Ieoka et al. | 348/71 |
| 5,749,830 A | * | 5/1998 | Kaneko et al. | 600/160 |
| 6,099,466 A | | 8/2000 | Sano et al. | |
| 6,219,091 B1 | * | 4/2001 | Yamanaka et al. | 348/65 |
| 6,293,911 B1 | * | 9/2001 | Imaizumi et al. | 600/160 |
| 6,371,908 B1 | * | 4/2002 | Furusawa et al. | 600/160 |
| 6,413,211 B2 | * | 7/2002 | Higuchi et al. | 600/181 |
| 6,527,708 B1 | * | 3/2003 | Nakamura et al. | 600/160 |
| 6,545,703 B1 | | 4/2003 | Takahashi et al. | |
| 6,663,561 B2 | | 12/2003 | Sugimoto et al. | |
| 7,450,151 B2 | * | 11/2008 | Kaneko | 348/72 |
| 2001/0055462 A1 | * | 12/2001 | Seibel | 385/147 |
| 2004/0037454 A1 | * | 2/2004 | Ozawa et al. | 382/128 |
| 2004/0257438 A1 | * | 12/2004 | Doguchi et al. | 348/65 |
| 2005/0182321 A1 | * | 8/2005 | Frangioni | 600/431 |
| 2005/0215854 A1 | * | 9/2005 | Ozaki et al. | 600/109 |
| 2006/0134001 A1 | * | 6/2006 | Frangioni | 424/9.6 |
| 2007/0203413 A1 | * | 8/2007 | Frangioni | 600/478 |

FOREIGN PATENT DOCUMENTS

| | | |
|---|---|---|
| JP | 9-066023 | 3/1997 |
| JP | 2002-112949 | 4/2002 |
| JP | 2003-033324 | 2/2003 |

* cited by examiner

*Primary Examiner*—John P Leubecker
*Assistant Examiner*—Samuel Candler
(74) *Attorney, Agent, or Firm*—Greenblum & Bernstein, P.L.C.

(57) ABSTRACT

An electronic endoscope system according to the present invention has a video-scope that has an image sensor, and a light source unit that is capable of selectively emitting normal-light and excitation-light. The electronic endoscope system further has a signal processor and a display processor. The signal processor generates normal color image signals, which corresponds to the normal color image, on the basis of the normal image-pixel signals. Similarly, the signal processor generates auto-fluorescent image signals corresponding to the auto-fluorescent image on the basis of the auto-fluorescent image-pixel signals, and generates diagnosis color image signals corresponding to the diagnosis color image on the basis of the normal color image signals and the auto-fluorescent image signals. The display processor processes the normal color image signals, the auto-fluorescent image signals, and the diagnosis color image signals so as simultaneously to display a normal color movie-image, an auto-fluorescent movie-image, and a diagnosis color movie-image.

14 Claims, 7 Drawing Sheets

MOVIE-IMAGE

FIG. 4B

FREEZE SCREEN

FIG. 5A

MOVIE-IMAGE

FIG. 5B

FREEZE SCREEN

FIG. 6

ELECTRONIC ENDOSCOPE SYSTEM

BACKGROUND OF THE INVENTION

1. Field of the Invention

The present invention relates to an electronic endoscope system that is capable of displaying a normal color image obtained by using a normal lamp emitting visible light, such as a xenon lamp, and an auto-fluorescent image for observing or diagnosing a lesion, such as a cancer. In particular, it relates to a display process for simultaneously displaying an auto-fluorescent image and a normal color image on a monitor.

2. Description of the Related Art

In an electronic endoscope system with an auto-fluorescent observation function, light, having a wavelength in the ultraviolet range or in that vicinity (hereinafter, called "excitation-light"), is emitted toward the epithelium of an organ such as the lungs. Tissue in the epithelial layer has a fluorescent substance, which emits fluorescent light (hereinafter, called "auto-fluorescent light") when the excitation-light is illuminated thereon. An object image is formed on an image sensor provided on a tip portion of a video-scope, due to the fluorescent light passing through an objective lens, so that an image based on fluorescent light (hereinafter, called an "auto-fluorescent image") is displayed on a monitor. Since the amount of auto-fluorescent light, which is emitted from a lesion or a piece of abnormal tissue, is weak compared to that emitted from the normal tissue, luminance of the lesion or the area adjacent to the lesion in an auto-fluorescent image is relatively small; thus, the lesion can be easily detected compared with a normal full color image obtained by white light emitted from a lamp such as a xenon lamp.

For example, consider a first image sensor for white light and a second image sensor for auto-fluorescent light which are equipped with the electronic endoscope simultaneously to display the normal color image and the auto-fluorescent image. Also, in the case of an electronic endoscope having one image sensor, white light and excitation-light are alternately emitted to simultaneously display the normal color image and the auto-fluorescent image. Further, to distinguish a lesion from a normal tissue, an image in which the lesion portion is colored (hereinafter, called a "pseudo-color image") is generated on the basis of the normal color image and the auto-fluorescent image. When displaying the pseudo-color image, a switch button provided on a video-scope or a video-processor is switched so that the normal image and/or the auto-fluorescent image are erased and the pseudo-color image is displayed.

SUMMARY OF THE INVENTION

An object of the present invention is to provide an electronic endoscope system that is capable of a normal color image, an auto-fluorescent image, and a so called "pseudo-color image"; namely, an diagnosis color image, which is a colored image to distinguish a lesion from other portion of the body.

An electronic endoscope system according to the present invention has a video-scope that has an image sensor, and a light source unit that is capable of selectively emitting normal-light and excitation-light. The normal-light is utilized for normal-observation; namely, for displaying a normal color observed image. The normal-light is usually white light, and the spectrum distribution is usually uniform over the wavelength of visible-light. Excitation-light is light used for emitting auto-fluorescent light from tissue in an epithelial layer, and has a specific wavelength. The wavelength of the excitation-light is basically in the range of ultraviolet light or visible light close to ultraviolet light. The excitation-light makes the tissue emit auto-fluorescent light, by which an auto-fluorescent image is formed. As for the illuminating method, the light source unit alternately emits the normal-light and the excitation-light. Consequently, image-pixel signals (herein, called "normal color image-pixel signals") obtained by the normal-light and image-pixel signals (herein, called "auto-fluorescent image-pixel signals") obtained by the auto-fluorescent light are alternately read from said image sensor, in that order. In the case of the NTSC or PAL standards, the normal color image-pixel signals and the auto-fluorescent image-pixel signals are alternately read from the image sensor at $\frac{1}{60}$ or $\frac{1}{50}$ second intervals.

The electronic endoscope system, further, has a signal processor, and a display processor. The signal processor generates normal color image signals, which correspond to the normal color image, on the basis of the normal color image-pixel signals Similarly, the signal processor generates auto-fluorescent image signals corresponding to the auto-fluorescent image on the basis of the auto-fluorescent image-pixel signals, and generates diagnosis color image signals corresponding to the diagnosis color image on the basis of the normal color image signals and the auto-fluorescent image signals. Based on the simultaneously generated above three image signals, the display processor processes the normal color image signals, the auto-fluorescent image signals, and the diagnosis color image signals so as simultaneously to display a normal color movie-image, an auto-fluorescent movie-image, and a diagnosis color movie-image. For example, the display processor processes the normal color image signals, the auto-fluorescent image signals, and the diagnosis color image signals so as to display the normal-color movie-image and the auto-fluorescent movie-image, while aligning the normal-color movie-image and the auto-fluorescent movie-image along one direction. The operator then diagnoses the lesion clarified by the three movie-images.

To display the diagnosis color image, for example, two memories and two switches are provided. Namely, the signal processor has first and second memories that store, respectively, the normal color image signals and the auto-fluorescent image signals, first and second switches that connect with said display processor, and first and second contacts that are provided, respectively, for transmitting the normal color image signals and the auto-fluorescent image signals The first switch alternately connects with said first memory and said first contact, at the field interval. The second switch alternately connects with said second memory and said second contact at the field interval. The first switch connects with said first contact while said second switch connects with said second memory.

To display the normal color image and the auto-fluorescent image, for example, the signal processor has third and fourth memories that store, respectively, the normal color image signals and the auto-fluorescent image signals, and a switch that connects with said display processor. The switch alternately connects with the third memory and the fourth memory at the frame interval.

When displaying a still image, an image-changing member is provided. The image changing member is operated to switch a movie-image mode for displaying the normal color movie-image, the auto-fluorescent movie-image, and the diagnosis color movie-image to a still image mode for displaying a normal color still-image, an auto-fluorescent still image, and a diagnosis color still image. The signal processor repeatedly feeds one frame-worth of normal color image signals corresponding to the normal color still image, one frame-worth of auto-fluorescent image signals corresponding to the auto-fluorescent still-image, and one frame-worth of diagnosis color image signals corresponding to the diagnosis color still-image, to said display processor. When displaying a movie-image in addition to still images, the signal processor generates the normal color image signals while displaying the normal color still-image, the auto-fluorescent still-image, and the diagnosis color still-image.

A method according to another aspect of the present invention is a method for displaying an observed image captured or acquired by a video-scope with an image sensor. The normal color image-pixel signals obtained by normal-light and auto-fluorescent image-pixel signals obtained by auto-fluorescent light are alternately read from said image sensor The method comprises: a) generating normal color image signals on the basis of the normal color image-pixel signals; b) generating auto-fluorescent image signals on the basis of the auto-fluorescent image pixel signals; c) generating diagnosis color image signals on the basis of the normal color image signals and the auto-fluorescent image signals; and d) processing the normal color image signals, the auto-fluorescent image signals, and the diagnosis color image signals so as to simultaneously display a normal color movie-image, an auto-fluorescent movie-image, and a diagnosis color movie-image that is a colored image for discriminating a lesion from other portion.

BRIEF DESCRIPTION OF THE DRAWINGS

The present invention will be better understood from the description of the preferred embodiments of the invention set forth below together with the accompanying drawings, in which.

DESCRIPTION OF THE PREFERRED EMBODIMENTS

Hereinafter, the preferred embodiment of the present invention is described with reference to the attached drawings.

Figure 1:
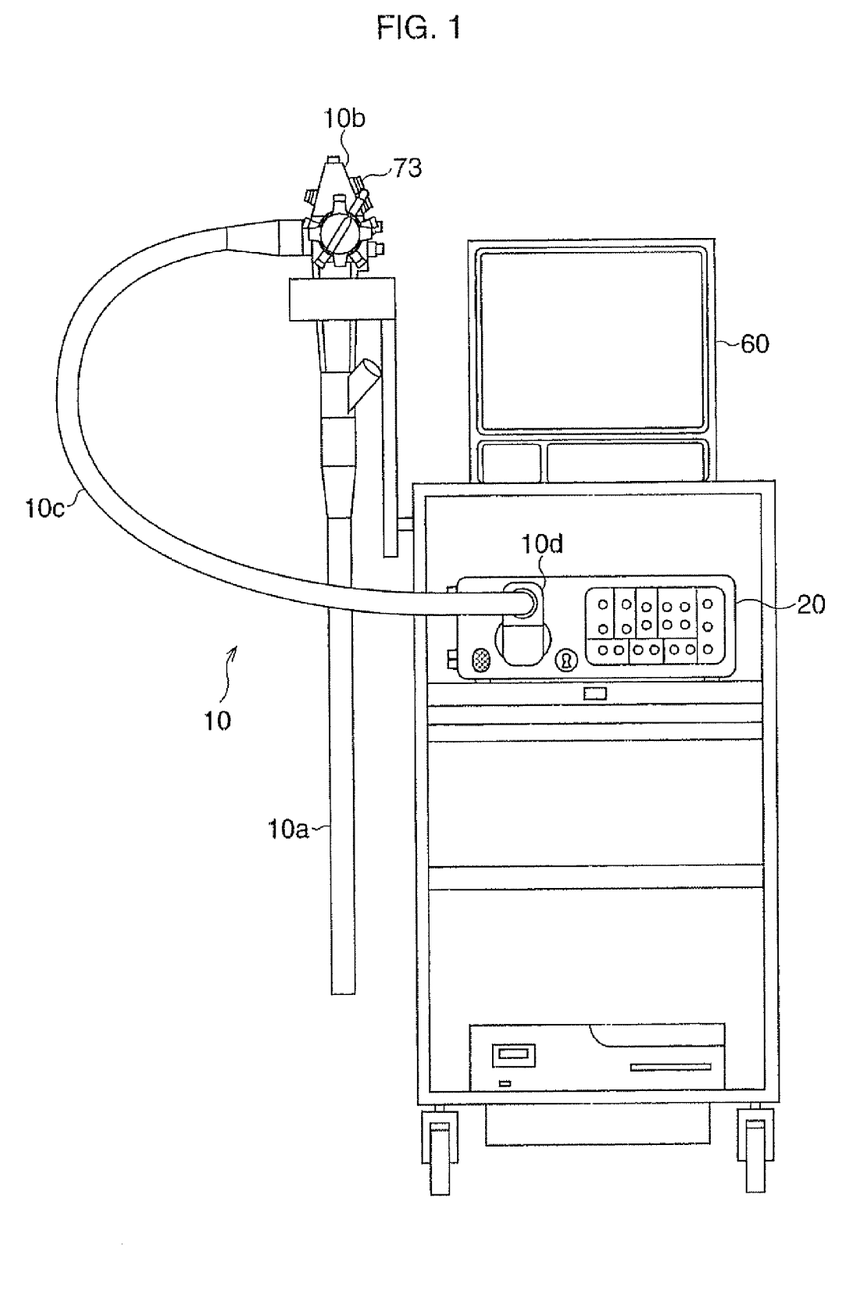
FIG. 1 is a schematic view of an electronic endoscope system.

FIG. 1 is a schematic view of an electronic endoscope system according to the present embodiment.

The electronic endoscope system having a video-scope 10, a video-processor 20 is an endoscope system that is capable of displaying an auto-fluorescent image. The video-scope 10 is constructed of a flexible, long and narrow inserted portion 10a, which has a winding portion at the end, an operated portion 10b that is operated to wind the winding portion, a cable 10c, and a connected portion 10d connected to the video-processor 20. A freeze button 73 is provided on the operated portion 10b, and is operated when displaying a still image on the monitor 60. A movie-image mode is set while the freeze button 73 of the operated portion 10b is not depressed, and a still-image mode is set while the freeze button 73 is depressed. When the connected portion 10d is connected to the video-processor 20 and an electric power button (not shown) provided on the video-scope 20 is turned ON, electric power is supplied from the video-processor 20 to the video-scope 10.

Figure 2:
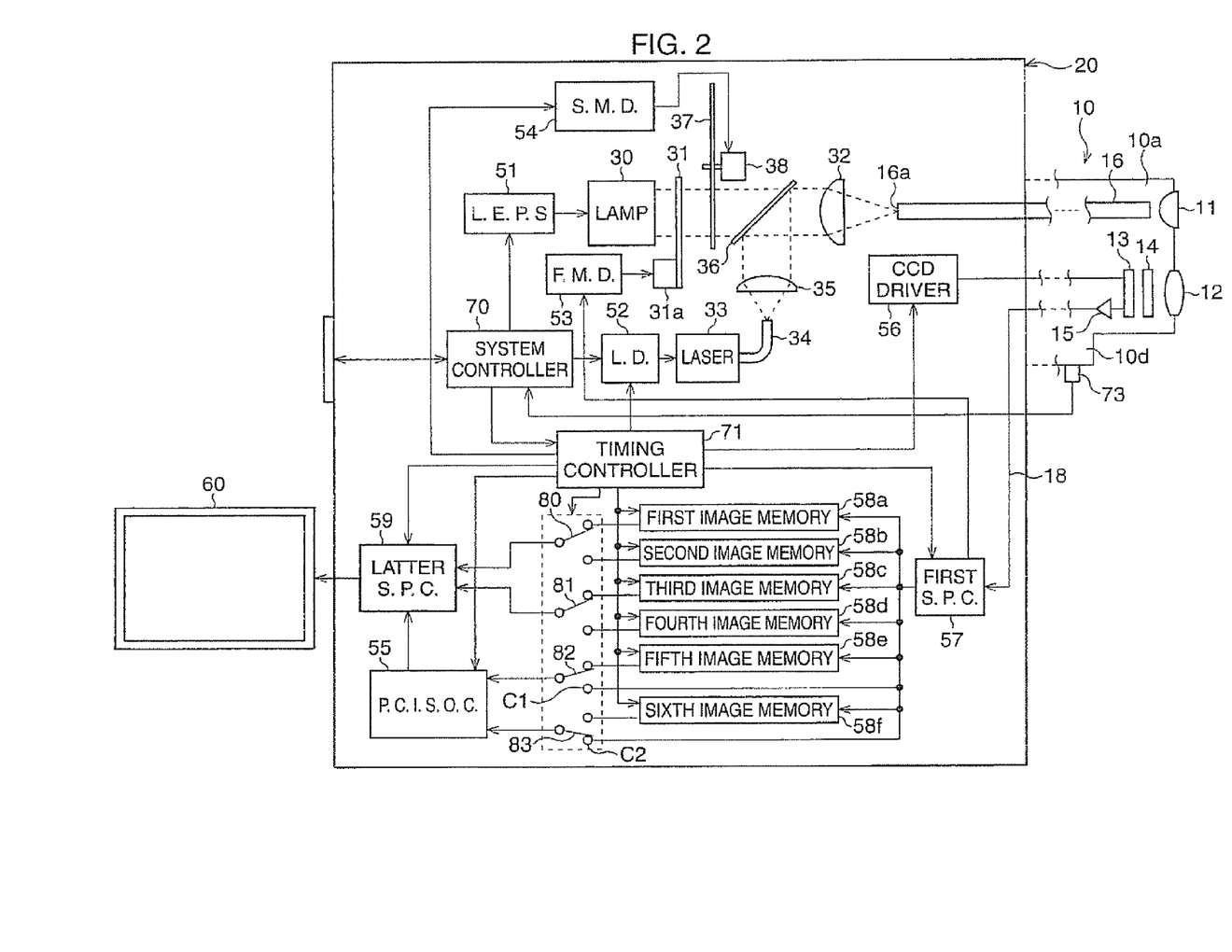
FIG. 2 is a block diagram of the electronic endoscope system.
Figure 3:
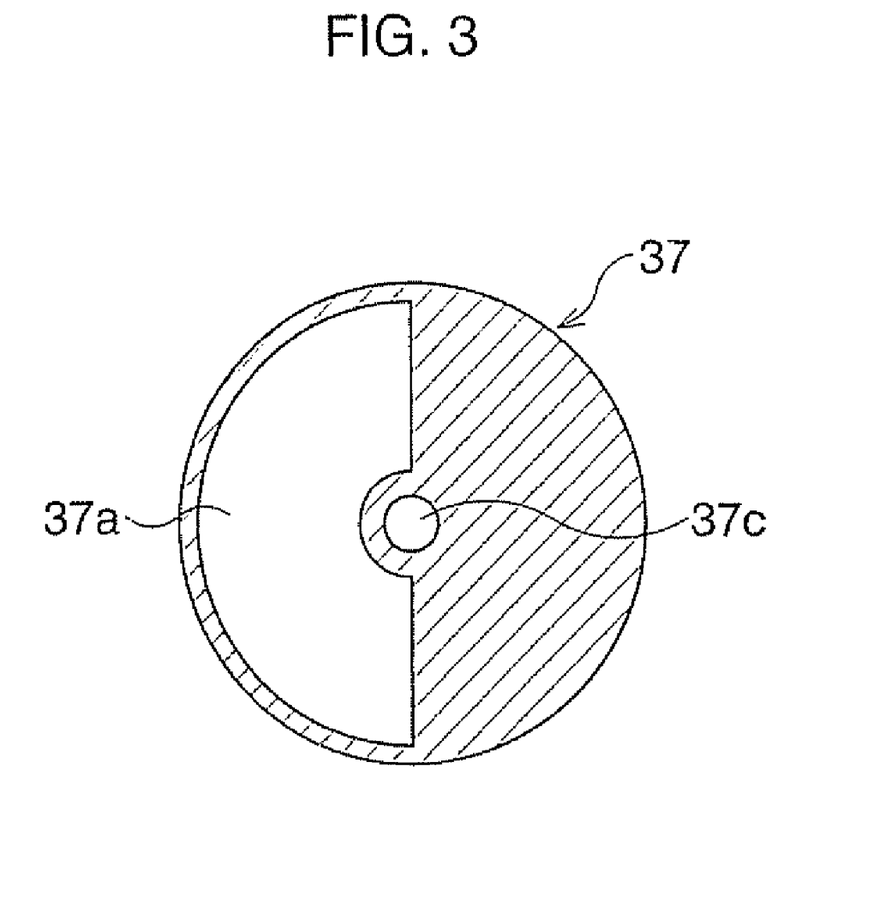
FIG. 3 is a plan view showing a rotary shutter.

FIG. 2 is a block diagram of the electronic endoscope system. FIG. 3 is a plan view showing a rotary shutter.

In the video-processor 20, a lamp 30 such as a xenon lamp, which emits white light, and a laser 33 such as a semiconductor laser, which emits excitation-light, are provided. The spectral distribution of the white light is generally uniform and spreads over the range of visible light. The excitation-light is light for emitting auto-fluorescent light from the tissue of the observed portion, and has a narrow specific wavelength or spectrum. The white light radiated from the lamp 30 enters an incident surface 16a of a light-guide 16 via a dichroic mirror 36, and a collecting lens 32. On the other hand, the laser beam emitted from the laser 33 passes a single optic-fiber 34, and enters into the incident surface 16a of the light-guide 16 via a collimator lens 35, the dichroic mirror 36, and the collecting lens 32. The lamp 30 and the laser 33 are respectively driven by a lamp electric power supply 51 and a laser driver 52.

The light-guide 16 of a fiber-optic bundle, which is provided in the video-scope 10, directs light to the tip portion of the video-scope 10. The light exiting from the light-guide 16 is emitted from the tip portion of the video-scope 10 via a diffusion lens 11, thus illuminating the observed portion. Light reflected off the object passes through an objective lens 12 and an excitation-light cut-off filter 14, so that the object image is formed on a photo-sensor area of a CCD 13, which is provided in the tip portion of the video-scope 10. The excitation-light eliminating filter 14 blocks or cuts off the excitation-light reflected from the observed portion.

In this embodiment, an on-chip color filter method using an on-chip color filter is applied. On the photo-sensor area of the CCD 13, a complementary color filter (not shown), checkered by four color elements, Yellow (Y), Magenta (Mg), Cyan (Cy), and Green (G), is arranged such that each area of the four color elements is opposite a pixel, and the pixels are two-dimensionally arranged in the photo-sensor area. In the CCD 13, image-pixel signals, corresponding to light passing through the complementary color filter, are generated by the photoelectric transform effect. Herein, image-pixel signals obtained by the white light (herein, called "normal color image-pixel signals") and image-pixel signals obtained by the auto-fluorescent light (herein, called "auto-fluorescent image-pixel signals") are generated.

A CCD driver 56 outputs clock pulse signals to the CCD 13 to read the image-pixel signals. The generated image-pixel signals are read from the CCD 13 at regular time intervals in accordance with a so called "color difference line sequential system." Herein, the NTSC or PAL standard is applied as the video-standard, thus one field worth of image-pixel signals are successively read from the CCD 13 at 1/60 or 1/50 second time intervals, and are then fed to a first signal processing circuit 57 via an amplifier 15.

In the first signal processing circuit 57, predetermined processes, such as a white balance process and a gamma correction process, are performed for the image-pixel signals. Consequently, digital image signals corresponding to the white light (hereinafter, called "normal color image signals"), and digital image signals corresponding to the auto-fluorescent light (hereinafter, called "auto-fluorescent image signals") are generated. The normal color image signals and the auto-fluorescent image signals are temporarily stored in a first image memory 58*a* and a second image memory 58*b* as data, and are fed to a latter signal processing circuit 59 via a first switch 80.

Further, the normal color image signals and the auto-fluorescent image signals are stored, respectively, in a fifth image memory 58*e* and a sixth image memory 58*f*, and are fed to a pseudo-color image signal operating circuit 55 via third and fourth switches 82 and 83. In the pseudo-color signal operating circuit 55, as described later, pseudo-color image signals are generated on the basis of the auto-fluorescent image signals and the normal color image signals. In the latter signal processing circuit 59 with a VRAM (not shown), a display process is performed so as to simultaneously display a normal color image, an auto-fluorescent image, and a pseudo color image on the monitor 60. When the freeze button 73 of the video-scope 10 is pressed to display a still image, the normal color signals, which are stored in third and fourth image memories 58*c* and 58*d*, are fed to the latter signal processing circuit 59 via a second switch 81.

A disk-shaped rotary shutter 37 has a semicircular-hole 37*a*, extending circumferentially, as shown in FIG. 3. The center of the rotary shutter 37C is coaxially attached to a motor 38, which rotates the rotary shutter 37 and is driven by a second motor driver 54. The rotary shutter 37 is arranged so as to cross a light-path of the light radiated from the lamp 30. While the rotary shutter 37 rotates by the rotation of the motor 38, the parallel white light, emitted from the lamp 30, is periodically intercepted by the rotary shutter 37.

The laser 33 emits the excitation-light, namely, a laser beam having a narrow wavelength in a range of wavelengths corresponding to the ultraviolet ray and visible rays close to the ultraviolet ray. The collimator lens 35 collimates the laser beam radiated from the laser 33, and the paralleled light is reflected on the dichroic mirror 36, which is inclined by 45 degrees relative to the light-path of the lamp 30 and the light-path of the laser beam. The reflected light is directed to the incident surface 16*a* of the light-guide 16 along the light-path of the lamp 30.

The motor 38 rotates such that the rotary shutter 37 rotates by one rotation in one frame-interval (⅓₀ or ⅟₂₅ second) and the emitted white light passes through the semicircular-hole 37*a* for the first (odd) field interval. On the other hand, the laser 33 emits the laser beams such that the excitation-light periodically is emitted only for the second (even) field interval. Thus, the white light and the excitation-light alternately illuminate the observed portion in each frame interval.

The first and second image memories 58*a* and 58*b* are used for displaying the normal color image and the auto-fluorescent image. The third and fourth image memories 58*c* and 58*d* are used for displaying a movie image in a situation in which a still image is displayed. The fifth and sixth image memories 58*e* and 58*f* are used for displaying the pseudo-color image. Each of image memories 58*a* to 58*f* is constructed of an SDRAM (Synchronous Dynamic Random Access Memory), wherein the reading and writing of data are separately carried out. The first and second image memories 58*a* and 58*b*, the third and fourth image memories 58*c* and 58*d*, and the fifth and sixth image memories 58*e* and 58*f* function, respectively, as pairs of image memories, which enable a successive reading and writing of image signals.

The first switch 80 selectively connects the first image memory 58*a* or the second image memory 58*b* with the latter signal processing circuit 59. Namely, the first switch 80 selectively transmits either the image signal stored in the first image memory 58*a* or the image signal stored in the second image memory 58*b*, to the latter signal processing circuit 59. Also, the second switch 81 selectively connects either the third image memory 58*c* or the fourth image memory 58*d* with the latter signal processing circuit 59. The third switch 82 selectively connects either the fifth memory 58*e* or a contact C1 with the latter signal processing circuit 59. Similarly, the fourth switch 83 selectively connects either the sixth image memory 58*f* or a contact C2 with the latter signal processing circuit 59.

A system controller 70 including a ROM chip, a RAM chip, and a CPU controls the video-processor 20, and outputs control signals to the laser driver 52, a timing controller 71, and so forth. When the freeze button 73 is pressed, control signals for displaying a still image are output to the timing controller 71 The timing controller 71 outputs clock pulse signals to each circuit in the video-process 20 to synchronize the input and output of signals in each circuit. The timing controller 71 controls the change of ON/OFF status for the laser 33 via the laser driver 52, and controls the rotation of the rotary shutter 37 via the second motor driver 54. Based on whether the freeze button 73 is pressed, the timing controller 71 controls the motion of the switches 80 to 83 A stop 31, provided between the lamp 30 and the rotary shutter 37, is driven by a motor 31*a* such that a brightness of the displayed object image is maintained with an adequate brightness The motor 31*a* is driven by a first motor driver 53.

Figure 4A:
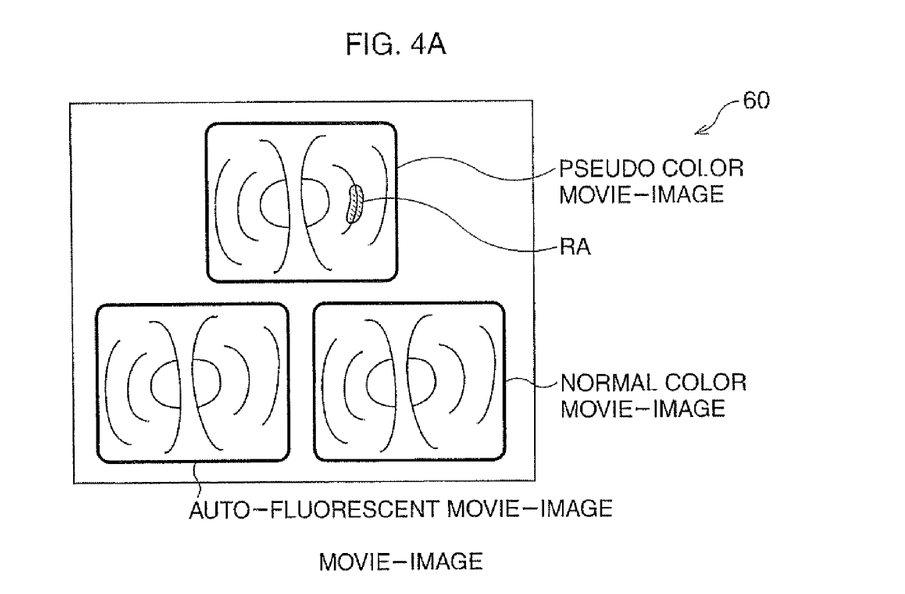
FIGS. 4A and 4B are views showing a screen on a monitor.
Figure 4B:
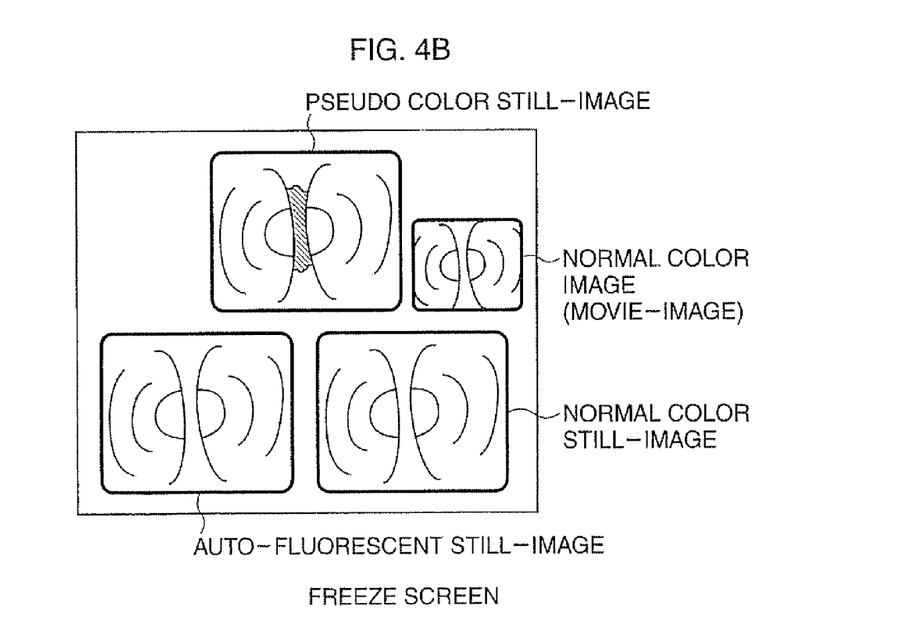

FIGS. 4A and 4B are views showing a screen on the monitor 60.

In FIG. 4A, a screen in a situation in which the movie-image mode is set, namely, in a situation in which the freeze button 73 is not depressed, is shown. As shown in FIG. 4A, the normal color movie-image, the auto-fluorescent movie-image represented by a gray-scale, and a pseudo-color movie-image for discriminating a lesion from the other portion are simultaneously displayed. The normal color image and the auto-fluorescent image are aligned in the lower portion of the screen, whereas the pseudo-color image is positioned in the middle of the upper portion of the screen. Herein, an area RA in the pseudo-color image is colored in red. The lesion is diagnosed through area RA distinguished from the other portion. When the freeze button 73 is depressed, a normal color still-image, an auto-fluorescent still-image, and a pseudo color still-image are displayed, as shown in FIG. 4B. Further, the normal color movie image is displayed at the side of the pseudo-color still-image.

Figure 5A:
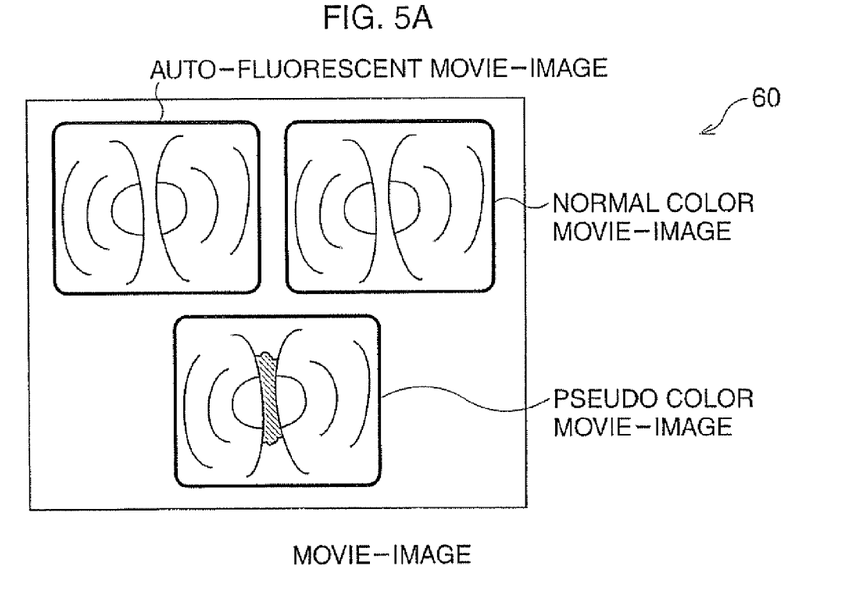
FIGS. 5A and 5B are views showing a screen different from the screen shown in FIGS. 4A and 4B.
Figure 5B:
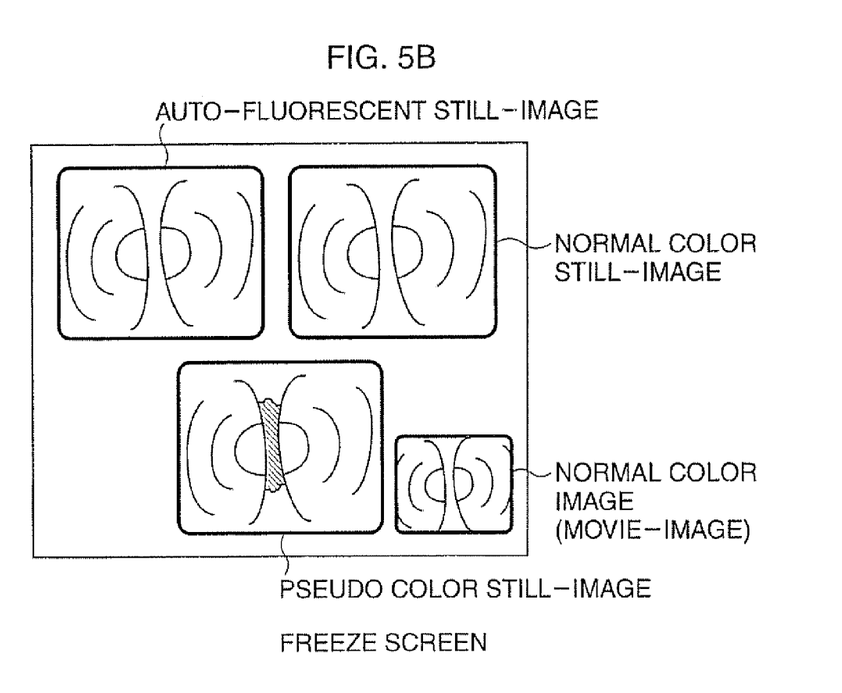

FIGS. 5A and 5B are views showing a screen different from the screen shown in FIGS. 4A and 4B. In FIGS. 5A and 5B, the normal color image and the auto-fluorescent image are displayed in the upper portion of the screen, whereas the pseudo-color image is displayed in the lower portion of the screen.

Figure 6:
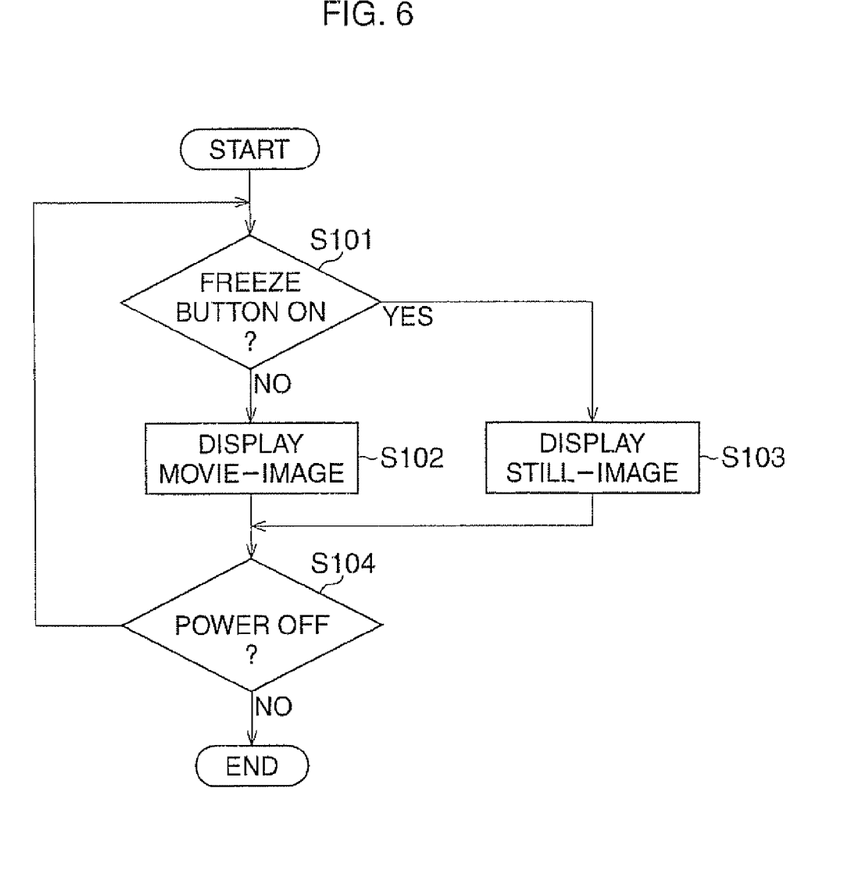
FIG. 6 is view showing a flowchart of a display process.
Figure 7:
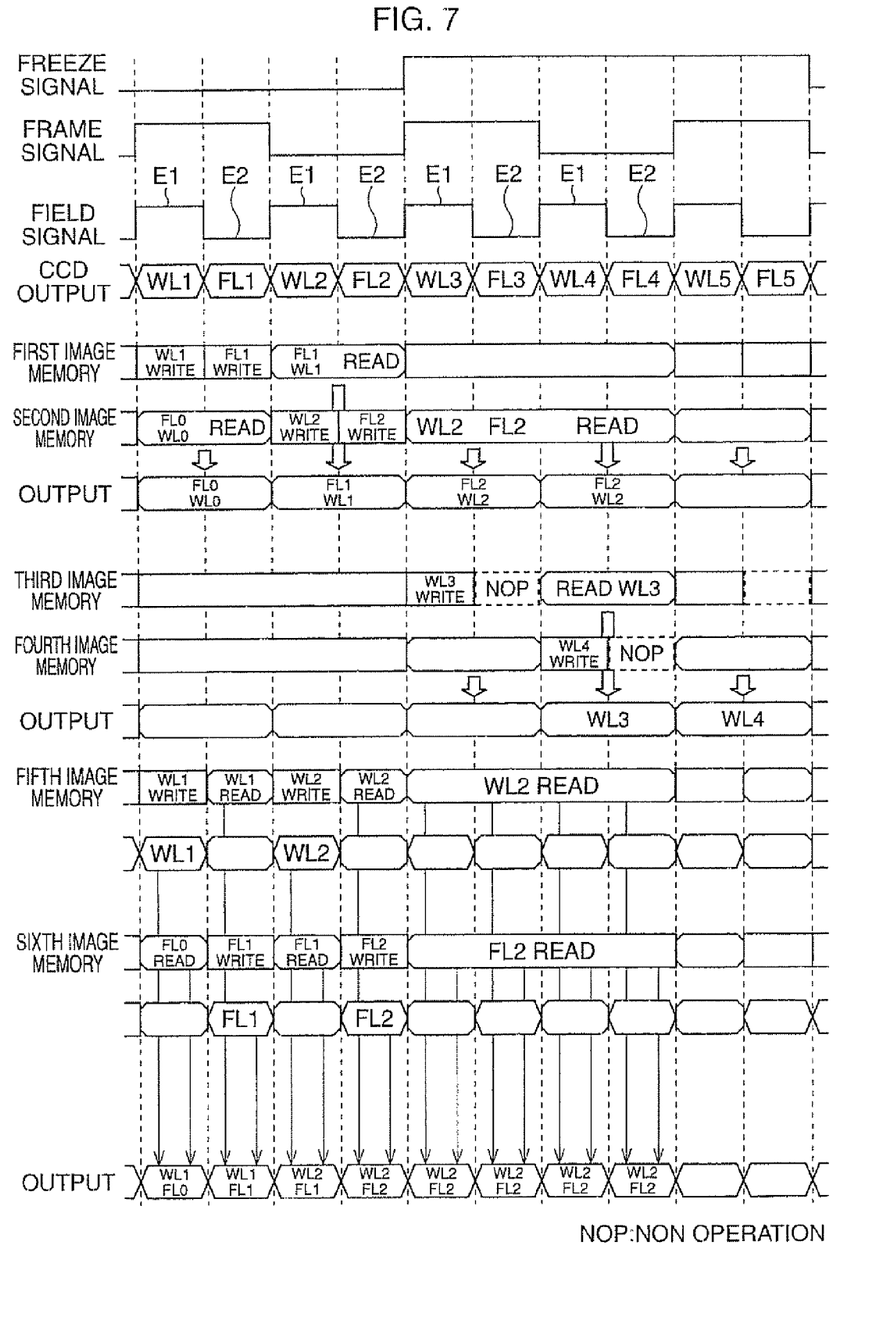
FIG. 7 is a view showing a timing chart of the display process.

FIG. 6 is a view showing a flowchart of a display process FIG. 7 is a view showing a timing chart of the display process.

In Step S101, it is determined whether the freeze button 73 is depressed to display the still images. When it is determined that the freeze button 73 is not depressed, the process goes to Step S102, wherein the movie-image mode is set, namely, the series of movie-images, the normal color image, the auto-fluorescent image, and the pseudo-color image are simultaneously displayed.

As described above, in the movie-image mode, the laser 33 and the rotary shutter 37 are controlled such that the white light and the excitation-light alternately illuminate the object at field (⅟₆₀ or ⅟₅₀ second) intervals Consequently, the normal color image-pixel signals and the auto-fluorescent image-pixel signals are read from the CCD 13 in order, over a one-frame interval. Then, the normal color signals and the auto-fluorescent image signals, which are generated in the first signal processing circuit 57, are stored or written in one of the first image memory 58a and the second image memory 58b over the one-frame interval.

When writing normal color image signals and auto-fluorescent image signals in one of the two image memories, normal color image signals and the auto-fluorescent image signals, which have been stored in the other memory, are read from the other memory. For example, as shown in FIG. 7, normal color image signals WL1 and auto-fluorescent image signals FL1 are stored in or written to the first image memory 58a. While writing the image signals WL1 and FL1 to the first image memory 58a, the first switch 80 shown in FIG. 2 connects the second image-memory 58b with the latter signal processing circuit 59, so that the normal color image signals WL0 and the auto-fluorescent image signals FL0, which have been stored in the second image memory 58b at the previous frame interval, are read from the second image memory 58b and are output to the latter signal processing circuit 59.

In the next frame interval, the writing and the reading are changed. Namely, the switch 80 connects the first image memory 58a with the latter signal processing circuit 59 so that the normal color image signals WL1 and the auto-fluorescent image signals FL1 are read from the first image memory 58a, whereas the next normal color image signals WL2 and auto-fluorescent image signals FL2 are written to the second image memory 58b.

To display the pseudo color image, the normal color image signals and the auto-fluorescent image signals are fed into the pseudo-color image signal operating circuit 55 at field intervals, as follows. The third switch 82 shown in FIG. 2 selectively connects either the fifth image memory 58e or the contact C1, both of which are connected to the first image signal processing circuit 57, with the pseudo-color image signal operating circuit 55, and alternately switches the connection in each field interval.

Specially, the third switch 82 connects with the contact C1 for the first (odd) field interval E1 (See FIG. 7), so that the normal color image signals are directly fed from the first signal processing circuit 57 to the pseudo-color image signal operating circuit 55, and, further, the normal color image signals are stored in the fifth image memory 58e. In the second (even) field interval E2, the third switch 82 connects with the fifth image memory 58e, so that the normal color image signals, which have been stored in the previous field interval, are read from the fifth image memory 58e and are fed to the pseudo-color image signal operating circuit 55. For example, in the first field interval E1, normal color image signals WL1 are stored in the fifth image memory 58e and are fed to the pseudo-color image signal operating circuit 55. In the second field interval E2, the normal color image signals WL1, which have been stored in the fifth image memory 58e, are fed to the pseudo-color signal processing operating circuit 55. Thus, the normal color image signals WL1 are continuously fed to the pseudo color image signal operating circuit 55 over one-frame intervals.

Similarly to the case with the third switch 82, the fourth switch 83 alternately connects with the sixth image memory 58f and the contact C2 connected to the first image signal processing circuit 57, at the field interval Note that the fourth switch 83 connects with the sixth image memory 58f during the first field interval E1. Therefore, the auto-fluorescent image signals generated in the second field interval E2 are directly fed from the first signal processing circuit 57 to the pseudo-color image signal operating circuit 55 and are stored in the sixth image memory 58f. On the other hand, in the first field interval E1, the auto-fluorescent image signals, which have been stored in the sixth image memory 58f, are fed to the pseudo-color image signal operating circuit 55. For example, in the first field interval E1, auto-fluorescent image signals FL0, which have been stored in the sixth image memory 58f in the previous field interval, are read from the sixth image memory 58f. In the second field interval E2, auto-fluorescent image signals FL1 are fed to the pseudo-color image signal operating circuit 55 and are stored in the sixth image memory 58f.

In the pseudo-color image signal operating circuit 55, the pseudo-color image signals are generated on the basis of the normal color image signals and the auto-fluorescent image signals, in accordance with a well known method. Each pixel in the auto-fluorescent image is divided or classified into a plurality of intensity levels or ranges, which are defined by the intensity of auto-fluorescent light, on the basis of a luminance value detected from the auto-fluorescent image signals. Herein, it is determined whether a level of the signal is less than a threshold value indicating a boundary between adjacent ranges, in each pixel. Thus, pixels having luminance values less than the threshold value are specified. The normal color image signals are processed such that specified pixels are colored on the normal color image, so that the pseudo-color image signals are generated. The generated pseudo-color image signals are fed to the latter signal processing circuit 59, and the pseudo-color image is displayed.

By these signal processes, the normal color image, the auto-fluorescent image, and the pseudo-color image are simultaneously displayed on the monitor 60. Note that, while the movie-image mode is set, the third and fourth memories 58c and 58d are not utilized.

On the other hand, when it is determined that the freeze button 73 is depressed so that a freeze switch (not shown) is turned ON in Step S101, the process goes to Step S103, wherein the still image mode is set, and the first switch 80 is controlled such that the writing to the first image memory 58a or the second image memory 58a or 58b, are prohibited. Further, the writing to the fifth and sixth image memories 58e and 58f are prohibited, namely, the third and fourth switches 82 and 83 are controlled so as to be connected with the fifth and sixth image memories 58e and 58f. Thus, the normal color image signals and the auto-fluorescent image signals, which have been stored in the previous frame interval, are repeatedly read from the first image memory 58a or the second image memory 58b, and the fifth and sixth image memories 58e and 58f. In FIG. 7, the first switch 80 connects with the second image memory 58b so that the normal color image signals WL2 and FL2 are continuously read from the second image memory 58b. Also, the third switch 82 and the fourth switch 83 respectively connect with the fifth image memory 58e and the sixth image memory 58f, so that the normal color image signals WL2 and the auto-fluorescent image signals FL2 are repeatedly read from the fifth image memory 58e and the sixth image memory 58f. Thus, the normal color still-image, the auto-fluorescent still-image, and the pseudo-color still-image are displayed as still images.

Further, to display a normal color movie-image in a small area, the normal color image signals are read from and written to the third image memory 58c and the fourth image memory 58d. For example, as shown in FIG. 7, the normal color image signals WL3 are written to the third memory 58c at the first field interval E1, whereas the third image memory 58c is not activated at the second field interval E2, in which the auto-fluorescent image signals are generated in the first signal processing circuit 57. Then, in the next frame interval, the normal color image signals WL3, which have been stored in the third image memory 58c at the previous frame interval, are read from the third image memory 58c. On the other hand, the next normal color image signals WL4 are stored in the fourth image memory 58*d* at the first filed interval E1. The fourth image memory 58*d* is not activated at the second field interval E2. By these processes, the normal color image signals and the auto-fluorescent image signals are successively fed to the latter signal processing circuit 59. When the freeze button 73 is released, the movie-image mode is set again In this way, in the present embodiment, the normal color image signals and the auto-fluorescent image signals are fed to the latter signal processing circuit 59 over one-frame intervals, whereas the pseudo-color image signals are fed to the latter signal processing circuit 59 at one-field intervals. Thus, the normal color movie-image, the auto-fluorescent movie-image, and the pseudo-color movie-image are simultaneously displayed on the monitor 60. Further, when the freeze button 73 is depressed, the normal color still-image, the auto-fluorescent still-image, and the pseudo-color still-image are displayed is displayed.

As for the memory, another memory such as a DRAM (Dynamic Random Access Memory) optionally can be utilized As for an arrangement of the three images, the normal color image, the auto-fluorescent image, and the pseudo-color image may be set in another arrangement instead of in the arrangement shown in FIG. 3.

Finally, it will be understood by those skilled in the arts that the foregoing description is of preferred embodiments of the device, and that various changes and modifications may be made to the present invention without departing from the spirit and scope thereof.

The present disclosure relates to subject matter contained in Japanese Patent Application No. 2005-142536 (filed on May 16, 2005), which is expressly incorporated herein, by reference, in its entirety.

The invention claimed is:

1. An electronic endoscope system, comprising:
    a light source unit that alternately emits normal-light and excitation-light at field intervals;
    a video-scope that has an image sensor, normal color image-pixel signals that are obtained while the normal-light is emitted and auto-fluorescent image-pixel signals that are obtained while the excitation-light is emitted both being alternately read from said image sensor;
    a signal processor that simultaneously generates, subsequent to the normal color image-pixels signals and auto-fluorescent image-pixels signals being read, normal color image signals on the basis of the normal color image-pixels signals, auto-fluorescent image signals on the basis of the auto-fluorescent image-pixel signals, and diagnosis color image signals on the basis of the normal color image signals and the auto-fluorescent image signals;
    a display processor that processes the normal color image signals, the auto-fluorescent image signals, and the diagnosis color image signals so as to simultaneously and separately display a normal color movie-image, an auto-fluorescent movie-image, and a diagnosis color movie-image that is a colored image for distinguishing a lesion from other portions of the body,
    wherein the signal processor performs writing and reading of normal color image signals to and from a first memory at field intervals, and performs writing and reading of auto-fluorescent image signals to and from a second memory at field intervals, so that the signal processor alternately writes the normal color image signals and the auto-fluorescent image signals, and wherein the signal processor transmits normal color image signals to a diagnosis color image signal processor that generates the diagnosis color images signals when reading the auto-fluorescent image signals from the second memory, whereas the signal processor transmits auto-fluorescent image signals to the diagnosis color image signal processor when reading the normal color image signals from the first memory,
    wherein said first memory and second memory respectively store the normal color image signals and the auto-fluorescent image signals, and
    wherein said signal processor has first and second switches that connect with said display processor, and first and second contacts that are provided, respectively, for transmitting the normal color image signals and the auto-fluorescent image signals, said first switch alternately connecting with said first memory and said first contact at the field interval, said second switch alternately connecting with said second memory and said second contact at the field interval, said first switch connecting with said first contact while said second switch connects with said second memory, and said second switch connecting with said second contact while said first switch connects with said first memory.

2. The electronic endoscope system of claim 1,
    wherein said signal processor has third and fourth memories that store, respectively, the normal color image signals and the auto-fluorescent image signals, and a switch that connects with said display processor, said switch alternately connecting with said third memory and said fourth memory at the frame interval.

3. The electronic endoscope of claim 2,
    wherein the signal processor transmits normal color image signals and auto-fluorescent color image signals, which are respectively stored in said third memory and said fourth memory, to the display processor at frame intervals.

4. The electronic endoscope system of claim 1, further comprising:
    an image-changing member that is operated to change a movie-image mode for displaying the normal color movie-image, the auto-fluorescent movie-image, and the diagnosis color movie-image to a still-image mode for displaying a normal color still-image, an auto-fluorescent still image, and a diagnosis color still image,
    wherein said signal processor feeds repeatedly one frame-worth of normal color image signals corresponding to the normal color still image, one frame-worth of auto-fluorescent image signals corresponding to the auto-fluorescent still-image, and one frame-worth of diagnosis color image signals corresponding to the diagnosis color still-image, to said display processor.

5. The electronic endoscope system of claim 4,
    wherein said signal processor further generates the normal color image signals while displaying the normal color still-image, the auto-fluorescent still-image, and the diagnosis color still-image.

6. The electronic endoscope system of claim 1,
    wherein said display processor processes the normal color image signals, the auto-fluorescent image signals, and the diagnosis color image signals so as to display the normal-color movie-image and the auto-fluorescent movie-image while aligning the normal-color movie-image and the auto-fluorescent movie-image along one direction.

7. The electronic endoscope system of claim 1,
    wherein said signal processor processes the normal color image signals and auto-fluorescent image signals such that pixels having luminance values less than a threshold level in auto-fluorescent image signals are colored in a normal color image.

8. The electronic endoscope of claim 1,
wherein the signal processor simultaneously generates the normal color image signals, auto-fluorescent image signals, and the diagnosis color image signals while the light source unit alternately emits normal-light and excitation-light at field intervals.

9. A video-processor that is connected to a video-scope with an image sensor, comprising:
a light source unit that alternately emits normal-light and excitation-light at field intervals, normal color image-pixel signals that are obtained while the normal-light is emitted and auto-fluorescent image-pixel signals that are obtained while the excitation-light is emitted, both being alternately read from said image sensor;
a signal processor that simultaneously generates, subsequent to the normal color image-pixels signals and auto-fluorescent image-pixels signals being read, normal color image signals on the basis of the normal color image-pixel signals, auto-fluorescent image signals on the basis of the auto-fluorescent image-pixel signals, and diagnosis color image signals on the basis of the normal color image signals and the auto-fluorescent image signals;
a display processor that processes the normal color image signals, the auto-fluorescent image signals, and the diagnosis color image signals so as to simultaneously and separately display a normal color movie-image, an auto-fluorescent movie-image, and a diagnosis color movie-image that is a colored image for distinguishing a lesion from other portions of the body,
wherein the signal processor performs writing and reading of normal color image signals to and from a first memory at field intervals, and performs writing and reading of auto-fluorescent image signals to and from a second memory at field intervals, so that the signal processor alternately writes the normal color image signals and the auto-fluorescent image signals, and wherein the signal processor transmits normal color image signals to a diagnosis color image signal processor that generates the diagnosis color image signals when reading the auto-fluorescent image signals from the second memory, whereas the signal processor transmits auto-fluorescent image signals to the diagnosis color image signal processor when reading the normal color image signals from the first memory,
wherein said memory and second memory respectively store the normal color image signals and the auto-fluorescent image signals, and
wherein said signal processor has first and second switches that connect with said display processor, and first and second contacts that are provided, respectively, for transmitting the normal color image signals and the auto-fluorescent image signals, said first switch alternately connecting with said first memory and said first contact at the field interval, said second switch alternately connecting with said second memory and said second contact at the field interval, said first switch connecting with said first contact while said second switch connects with said second memory, and said second switch connecting with said second contact while said first switch connects with said first memory.

10. The video-processor of claim 9,
wherein the signal processor transmits normal color image signals and auto-fluorescent color image signals, which are respectively stored in a third memory and a fourth memory, to the display processor at frame intervals.

11. An apparatus for displaying an observed image captured by a video-scope with an image sensor following normal-light and excitation-light being alternately emitted from a light source unit at field intervals, and normal color image-pixel signals that are obtained while the normal-light is emitted and auto-fluorescent image-pixel signals that are obtained while the excitation-light is emitted, both being alternately read from said image sensor, said apparatus comprising:
a signal processor that simultaneously generates, subsequent to the normal color image-pixel signals and auto-fluorescent image-pixel signals being read, normal color image signals on the basis of the normal color image-pixel signals, auto-fluorescent image signals on the basis of the auto-fluorescent image-pixel signals, and diagnosis color image signals on the basis of the normal color image signals and the auto-fluorescent image signals;
a display processor that processes the normal color image signals, the auto-fluorescent image signals, and the diagnosis color image signals so as to simultaneously and separately display a normal color movie-image, an auto-fluorescent movie-image, and a diagnosis color movie-image that is a colored image for distinguishing a lesion from other portions of the body,
wherein the signal processor performs writing and reading of the normal color image signals to and from a first memory at field intervals, and performs writing and reading of auto-fluorescent image signals to and from a second memory at field intervals, so that the signal processor alternately writes the normal color image signals and the auto-fluorescent image signals, and wherein the signal processor transmits normal color image signals to a diagnosis color image signal processor that generates the diagnosis color image signals when reading the auto-fluorescent image signals from the second memory, whereas the signal processor transmits auto-fluorescent image signals to the diagnosis color image signal processor when reading the normal color image signals from the first memory,
wherein said first memory and second memory respectively store the normal color image signals and the auto-fluorescent image signals, and
wherein said signal processor has first and second switches that connect with said display processor, and first and second contacts that are provided, respectively, for transmitting the normal color image signals and the auto-fluorescent image signals, said first switch alternately connecting with said first memory and said first contact at the field interval, said second switch alternately connecting with said second memory and said second contact at the field interval, said first switch connecting with said first contact while said second switch connects with said second memory, and said second switch connecting with said second contact while said first switch connects with said first memory.

12. The apparatus of claim 11,
wherein the signal processor transmits normal color image signals and auto-fluorescent color image signals, which are respectively stored in a third memory and a fourth memory, to the display processor at frame intervals.

13. A method for displaying an observed image captured by a video-scope with an image sensor following normal-light and excitation-light being alternately emitted from a light source unit at field intervals, and normal color image-pixel signals that are obtained while the normal-light is emitted and auto-fluorescent image-pixel signals that are obtained while the excitation-light is emitted both being alternately read from said image sensor, said method comprising:

generating, using a signal processor, normal color image signals on the basis of the normal color image-pixel signals and subsequent to the normal color image-pixel signals and auto-fluorescent image-pixels signals being read;

generating, using the signal processor and simultaneous with generating the normal color image signals, auto-fluorescent image signals, on the basis of the auto-fluorescent image-pixel signals and subsequent to the normal color image-pixel signals and auto-fluorescent image-pixel signals being read;

generating, using the signal processor and simultaneous with generating the normal color image signals and auto-fluorescent image signals, diagnosis color image signals, on the basis of the normal color image signals and the auto-fluorescent image signals and subsequent to the normal color image-pixel signals and auto-fluorescent image-pixel signals being read;

processing the normal color image signals, the auto-fluorescent image signals, and the diagnosis color image signals so as to simultaneously and separately display a normal color movie-image, an auto-fluorescent movie-image, and a diagnosis color movie-image that is a colored image for distinguishing a lesion from other portions of the body, performing, using the signal processor, writing and reading of normal color image signals to and from a first memory at field intervals, and performing writing and reading of auto-fluorescent image signals to and from a second memory at field intervals, so that the signal processor alternately writes the normal color image signals and the auto-fluorescent image signals, transmitting, from the signal processor, normal color image signals to a diagnosis color image signal processor that generates the diagnosis color image signals when reading the auto-fluorescent image signals from the second memory, and transmitting, from the signal processor, auto-fluorescent image signals to the diagnosis color image signal processor when reading the normal color image signals from the first memory, wherein said first memory and second memory respectively store the normal color image signals and the auto-fluorescent image signals, and wherein said signal processor has first and second switches that connect with said display processor, and first and second contacts that are provided, respectively, for transmitting the normal color image signals and the auto-fluorescent image signals, said first switch alternately connecting with said first memory and said first contact at the field interval, said second switch alternately connecting with said second memory and said second contact at the field interval, said first switch connecting with said first contact while said second switch connects with said second memory, and said second switch connecting with said second contact while said first switch connects with said first memory.

14. The method of claim 13,
wherein the normal color image signals and auto-fluorescent color image signals are respectively stored in a third memory and a fourth memory and transmitted by the signal processor to a display processor at frame intervals.

* * * * *